US010729896B2

(12) United States Patent
Gardner

(10) Patent No.: US 10,729,896 B2
(45) Date of Patent: Aug. 4, 2020

(54) DELIVERY AND INDUCTION OF THERAPEUTIC AGENTS AND USES THEREOF

(71) Applicant: Avidas Pharmaceuticals LLC, Doylestown, PA (US)

(72) Inventor: Margaret M. Gardner, Gladwyne, PA (US)

(73) Assignee: Avidas Pharmaceuticals LLC, Doylestown, PA (US)

( * ) Notice: Subject to any disclaimer, the term of this patent is extended or adjusted under 35 U.S.C. 154(b) by 108 days.

(21) Appl. No.: 15/513,304

(22) PCT Filed: Sep. 11, 2015

(86) PCT No.: PCT/US2015/049723
§ 371 (c)(1),
(2) Date: Mar. 22, 2017

(87) PCT Pub. No.: WO2016/048689
PCT Pub. Date: Mar. 31, 2016

(65) Prior Publication Data

US 2017/0304601 A1 Oct. 26, 2017

Related U.S. Application Data

(60) Provisional application No. 62/054,255, filed on Sep. 23, 2014.

(51) Int. Cl.
*A61N 1/30* (2006.01)
*A61M 37/00* (2006.01)
*A61N 1/32* (2006.01)
*A61N 1/44* (2006.01)

(52) U.S. Cl.
CPC ............. *A61M 37/00* (2013.01); *A61N 1/327* (2013.01); *A61N 1/44* (2013.01); *A61M 2037/0007* (2013.01)

(58) Field of Classification Search
CPC .......... A61M 2037/0007; A61M 37/00; A61N 1/327; A61N 1/44
See application file for complete search history.

(56) References Cited

U.S. PATENT DOCUMENTS

2013/0345620 A1* 12/2013 Zemel .................. A61B 18/042 604/24
2014/0188071 A1* 7/2014 Jacofsky .................. A61N 1/44 604/501

* cited by examiner

*Primary Examiner* — Rebecca E Eisenberg
(74) *Attorney, Agent, or Firm* — Lange IP Law

(57) ABSTRACT

Described are methods and therapeutic compositions and combinations for treating and/or preventing medical conditions, by application of non-thermal plasma to the skin. Also described are methods and compositions for treating and/or preventing various medical conditions, by application of non-thermal plasma to the skin, followed by topical application of a therapeutic composition.

16 Claims, No Drawings

DELIVERY AND INDUCTION OF THERAPEUTIC AGENTS AND USES THEREOF

RELATED APPLICATION DATA

This application is the U.S. National Phase of International Application No. PCT/US2015/049723, filed Sep. 11, 2015, which designed the U.S., which claims priority to U.S. provisional patent application No. 62/054,255, filed on Sep. 23, 2014, the entirety of which applications are hereby incorporated by reference in their entirety.

FIELD OF THE INVENTION

The present invention relates to methods and compositions useful for skin resurfacing and skin remodeling, as well as for the improved topical delivery and induction of therapeutic compositions, in particular with respect to side effects.

BACKGROUND OF RELATED TECHNOLOGY

Delivery systems, such as for pharmaceutical agents, include lipid vesicles, which require steroids, oils and charge-producing agents (e.g., oleic acid, dactyl phosphate, cetyl sulphate, phosphatidic acid, phosphatidyl serine, and/or mixtures thereof) for their formation (see, for example, U.S. Pat. No. 4,911,928 to Wallach; Ref. 1); and micellar nanoparticles, which contain oils and require initiators (see, for example, U.S. Pat. No. 5,629,021 to Wright; Ref. 2).

As is known to those in the art, delivery and induction of therapeutic agents through topical application has various limitations as a result of the carrier system, the type of compound and/or ingredient, solubility and size of the molecules in addition to the condition of the skin (wounded, damaged, aged, etc.). As is known in the art, conventional carrier systems (e.g., liposomes, transfersomes, nanoparticles) have various drawbacks as a result of ingredients used in their compositions and/or formulations. This is of particular importance when combining ingredient(s) delivery and induction with certain medical treatments, where delivery or induction is often not possible due to the often-damaged condition of the skin or tissue, due to an increased risk of infection and inflammation to the patient.

Delivery and induction of therapeutic topical ingredient(s) is also often not achieved at the desired level of absorption as therapy is often delayed until the damaged and/or wounded skin has healed. The delay in inducting and delivering therapeutic ingredient(s) to damaged and/or injured skin is largely due to the ingredient used in the formation of the topical delivery (chemical enhancers, steroids, etc.) which often irritate the skin and create side effects such as burning, erythema, drying and allergic reactions. Topical deliveries with pharmaceutical carriers such as nanoparticles and delivery systems with chemical enhancers have limitations as harmful ingredients may be delivered through the skin together with the desired ingredient(s).

Delivery of therapeutic ingredients is of particular importance in the field of dermatology. Skin conditions, disorders and diseases are often treated with concomitant treatments using topical delivery treatments with skin resurfacing and skin remodeling treatments such as lasers and other energy treatments, chemical peels, needling, thermal light treatments, etc. As is known in the art, conventional skin resurfacing treatments have various drawbacks including purpura, erythema, blistering, crusting, hyperpigmentation, hypopigmentation, thermal damage through heat treatments or pore punching methods of lasers; chemical peels; nano needles and other ablative and non-ablative therapies making induction and delivery of therapeutic ingredients in conjunction with resurfacing a challenge and dangerous. Depending on the type of skin resurfacing and remodeling, the downtime for skin healing (erythema, burns, blisters, etc.) may require days, weeks or longer. Combining these treatment modalities is highly desired in the clinical setting, Due to the impaired condition of the skin and the drawbacks of current topical delivery systems, combining these treatment modalities often result in increased side effects such as burning, itching swelling and erythema, worsening the risk for increased inflammation and infection with little to no delivery enhancement.

Accordingly, there is a need in the art for new and improved delivery systems, particularly for the delivery and induction of pharmaceutical ingredients, and for improved induction and delivery of pharmaceutical ingredients combined with skin resurfacing and skin remodeling with fewer side effects. It is therefore objects of the present invention to provide such delivery systems, as well as methods for using the same.

SUMMARY OF THE INVENTION

Generally speaking, the present invention addresses certain problems and needs in the art by providing improved methods of treating and/or preventing medical conditions in a patient in need thereof, by application of non-thermal plasma to the skin of the patient, wherein the non-thermal plasma application results in the resurfacing or the remodeling of the skin of the patient.

In certain non-limiting embodiments, the non-thermal plasma is delivered by high voltage energy positioned between an electrode and the skin, for example the electrode may be positioned on or above the skin.

In certain non-limiting embodiments, the non-thermal plasma application results in one or more of the following benefits to the patient: improvements to skin and scalp conditions, including improved moisture retention, improved elasticity, production of elastin, fibroblast and collagen and firmness; and anti-aging benefits, including improvements with respect to wrinkles, rhytides, lax skin, pigmentation and tattoo issues, vascular lesions, cellulite and fat deposits, insufficient and excess hair.

In certain non-limiting embodiments, the skin restructuring or remodeling resulting from application of the non-thermal plasma disrupts the skin tissue without creating holes or thermal damage to the outer skin.

In certain non-limiting embodiments, the skin restructuring or remodeling resulting from application of the non-thermal plasma enhances the health of the skin.

In certain non-limiting embodiments, methods of the present invention further include topical administration of a therapeutic composition to the skin of the patient following the non-thermal plasma application.

In certain non-limiting embodiments, topical application of the therapeutic composition may occur before, during or after the application of non-thermal plasma, and may include continuous or repeat applications.

In certain non-limiting embodiments, the therapeutic composition is topically administered in a single application, or is topically administered in multiple applications.

In certain non-limiting embodiments, the therapeutic composition includes an active ingredient which is present in the therapeutic composition in a therapeutically effective amount, and a pharmaceutical carrier effective for topical administration of the active ingredient.

In certain non-limiting embodiments, topical administration of the therapeutic composition results in an increase in the amount of the active agent in the patient's blood serum.

In certain non-limiting embodiments, the active agent is encapsulated.

In certain non-limiting embodiments, the therapeutically effective amount of the active ingredient is an amount sufficient to compensate for a reduction in the patient's natural production of the active ingredient or an insufficiency in the presence of the active ingredient in the patient.

In certain non-limiting embodiments, the active ingredient is selected from the group consisting of cosmetic ingredients, pharmaceutical ingredients, nutritional ingredients, minerals, vitamins, steroids, stimulants, stem cells, biologic ingredients, combinations, active forms and metabolites thereof.

In certain non-limiting embodiments, the therapeutic composition is in the form of a cream, gel, liquid, lotion, solution, spray, emulsion, serum, aerosol, foam, or a combination thereof.

In certain non-limiting embodiments, the pharmaceutically effective carrier is selected from the group consisting of intradermal and transdermal carriers such as water, organic compounds or mixtures thereof, liposomes, nanosomes, nanoparticles, micelles, transfersomes, multi-lamellar vesicles, and/or other pharmaceutical carriers.

In certain non-limiting embodiments, the pharmaceutically effective carrier is selected from the group consisting of water, alcohol, organic compounds, steroids, oils, lipids and phospholipids.

In certain non-limiting embodiments, the pharmaceutically effective carrier is an oil-free carrier.

In certain non-limiting embodiments, the pharmaceutically effective carrier is substantially free of a skin penetration enhancer or an initiator compound.

In certain non-limiting embodiments, the therapeutic composition further includes one or more emollients, skin conditioning agents, pH stabilizing agents, humectants, buffering agents, viscosity adjusting agents, preservatives, chelating agents, emulsifying agents, conditioning agents, thickening agents, wetting agents, antioxidants, UV stabilizers, UV radiation absorbers, sun-protecting ingredients, hyaluronic acid and other cosmetic acids, proteins, botulinum toxin, micronutrients, minerals and/or vitamins and their derivatives, proteins, steroids or stimulants, biologic ingredients, stem cells, fragrances, flavors or colorants.

In certain non-limiting embodiments, the non-thermal plasma application enhances the delivery or induction of the therapeutic composition to the skin of the patient.

In certain non-limiting embodiments, the non-thermal plasma application enhances the delivery or induction of the pharmaceutical carrier to the skin of the patient.

In certain non-limiting embodiments, the non-thermal plasma application enhances the delivery or induction of the active ingredient to the skin of the patient.

In certain non-limiting embodiments, the non-thermal plasma application enhances the delivery or induction of the therapeutic composition, pharmaceutical carrier and/or active agent to the skin of a patient due to a temporary remodeling or shifting of the skin cells for a period of time.

In certain non-limiting embodiments, the medical condition is selected from the group consisting of acne, psoriasis, and eczema, vitiligo, dermatitis, superficial lesions, actinic keratosis, seborrheic keratosis, lentigos, anti-aging including wrinkles, rhytides, pigmentation, redness, skin texture, tightness, scarring, pigmentation issues such as uneven pigmentation, melasma, pigmented lesions and tattoos, rebuilding collagen, elastin and overall skin rejuvenation; hair follicles and melanin stimulation or retardation of growth; fat and cellulite; vascular lesions such as birth marks, facial veins and rosacea, spider and varicose veins.

In certain non-limiting embodiments, the non-thermal plasma is administered to the patient in a single or in multiple applications.

In certain non-limiting embodiments, the present invention is directed to a device for treating and/or preventing a medical condition in a patient in need thereof, which is configured for application of non-thermal plasma to the skin of the patient, and results in the resurfacing or the remodeling of the patient's skin.

In certain non-limiting embodiments, the present invention is directed to pharmaceutical combinations that include (i) a device for treating and/or preventing a medical condition in a patient which is configured for application of non-thermal plasma to the skin of the patient, and results in the resurfacing or the remodeling of the patient's skin; and (ii) a therapeutic composition.

In certain non-limiting embodiments, application of the non-thermal plasma to the skin of the patient results in reduced side effects compared to application of thermal plasma to the skin of the patient.

In certain non-limiting embodiments, application of the non-thermal plasma to the skin of the patient is non-ablative.

In certain non-limiting embodiments, the present invention is directed to methods of treating and/or preventing a medical condition, disorder or disease in a patient in need thereof, which includes (i) application of non-thermal plasma to the skin of the patient, which results in the resurfacing or the remodeling of the skin of the patient; and (b) topical administration of a therapeutic composition to the skin of the patient following the non-thermal plasma application.

In certain non-limiting embodiments, the patient's medical condition is selected from the group consisting of: dermatological conditions, disorders and diseases, bone-related disorders and diseases including osteopenia, osteomalacia, osteoporosis, vitamin and nutritional disorders, autoimmune disorders or diseases including multiple sclerosis, fibromyalgia, rheumatoid arthritis, Graves disease and lupus, periodontal disorders and/or diseases; chronic pain; vascular disorders; seasonal affective disorders; cognitive impairment; depression; diabetes; chronic renal disease; cardiovascular and metabolic disorders and/or diseases; certain types of cancers including breast cancer, prostate cancer, colon cancer, pancreatic cancer and skin cancer.

DETAILED DESCRIPTION OF THE INVENTION

Generally speaking, and as discussed in greater detail in the illustrative and non-limiting examples provided herein, the present invention is directed to non-thermal plasma skin resurfacing/skin remodeling and topical delivery and induction of therapeutic ingredients with relatively fewer side effects for treating and/or preventing medical conditions, disorders and diseases.

In certain exemplary, non-limiting embodiments, the inventive topical and non-thermal plasma deliveries enhance delivery of therapeutic ingredients or compounds without the need for chemical enhancers or nanoparticles for penetration and with minimal to no side effects. It is understood that the inventive compositions may be administered separately or in combination to any mammal in which they are effective and are particularly useful in mammals suited for intradermal and transdermal drug delivery (such as humans, pigs and so forth). Therefore, the terms "mammal(s)", "individual(s)" and so forth as used herein are non-limiting and are to be construed broadly.

In certain exemplary, non-limiting embodiments, the inventive topical and non-thermal plasma deliveries improve skin conditions in mammals when treatments are administered separately or in combination.

In certain exemplary, non-limiting embodiments, the inventive topical and non-thermal plasma deliveries are used to prevent and/or treat conditions, disorders and/or diseases, for example and without limitation, dermatological conditions, disorders and diseases, bone-related disorders and diseases including osteopenia, osteomalacia, osteoporosis, vitamin and nutritional disorders including fat and water soluble, autoimmune disorders or diseases including multiple sclerosis, fibromyalgia, rheumatoid arthritis, Grave's disease and lupus, periodontal disorders and/or diseases; chronic pain; vascular disorders; seasonal affective disorders; cognitive impairment; depression; diabetes; chronic renal disease; cardiovascular and metabolic disorders and/or diseases; certain types of cancers including breast cancer, prostate cancer, colon cancer, pancreatic cancer and skin cancer.

In certain non-limiting embodiments, the inventive topical and non-thermal plasma deliveries used to prevent and/or treating medical conditions, disorders and/or diseases, for example and with limitation, acne, psoriasis, eczema, vitiligo, dermatitis, superficial lesions, actinic keratosis, seborrhoeic keratosis, lentigos, anti-aging including wrinkles, rhytides, pigmentation, redness, skin texture, tightness, scarring, pigmentation issues such as uneven pigmentation, melasma, pigment lesions and tattoos, rebuilding collage, elastin and overall skin rejuvenation; hair follicles and melanin to stimulation or retardation of growth; fat and cellulite; vascular lesions such as birthmarks, facial veins and rosacea, spider and varicose veins.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions and usages provided herein take precedent over any dictionary or extrinsic definition. That the present invention may be more readily understood, select terms are defined herein according to their usage.

As used herein, a "therapeutically effective amount" of a particular compound or ingredient refers, for example and without limitation, to an amount of such compound or ingredient that is effective to achieve a desired therapeutic result at a particular dosage, according to a particular dosing regimen, and over a particular period of time. The amount of a compound or ingredient necessary, to achieve a desired therapeutic result is influenced by, and will therefore vary based on, a number of factors, including for example and without limitation, the age, sex and weight of the individual, factors that influence the metabolic rate of an individual, and any disorders or diseases of the individual (including the degree and severity thereof). Dosing regimens may therefore be adjusted to achieve a desired therapeutic effect for a given individual. A "therapeutically effective" amount also refers to an amount at which negative factors, such as side effects and/or tolerance and/or toxicity resulting from administration of the compound or ingredient, are outweighed by the benefits provided by administration of the compound.

As used herein, for example and without limitation, a "therapeutically effective amount" of a particular compound or ingredient refers to an amount which may be determined using histological measurements or pharmacokinetic analysis and techniques known to those of skill in the art. In various embodiments achieving a therapeutically effective amount will take into account various factors, for example and with limitation, that such compositions or formulations may be exposed to water including alkaline salt water, may be partially removed by "towel drying" or "wiping off" after a period of time, and so forth, and therefore in such embodiments such factors may be taken into account to ensure that a therapeutically effective amount is administered to the individual, for example and without limitation, the concentration of the ingredient, the delivery mechanism and the inclusion of specific ingredients such as stabilizers, wetting solutions, preservatives, sun-protecting ingredients, and so forth. In certain embodiments, it may be intended that the inventive compositions or formulations be re-applied after a certain period of time for particular therapeutic purposes, which will be taken into account in determining the concentration of the ingredients present in such compositions or formulations.

By way of further example and without limitation, a "therapeutically effective amount" present in the inventive deliveries is one in which improvement is realized with respect to one or more conditions, disorders and/or disease states in an individual. Such conditions, disorders and disease states include, for example and without limitation, all known conditions, disorders and disease states regardless of whether due to environment, dietary and/or physiological factors and/or genetic and/or natural aging process.

By way of further example and without limitation, a "therapeutically effective amount" present in the inventive deliveries is one administered to an individual in order to replace or increase ingredients or compounds made naturally such as micronutrients, proteins, minerals and/or vitamins or is administered to an individual in order to achieve a particular therapeutic benefit. It is understood that those of ordinary skilled in the art will, based on the teachings herein, be capable of empirically determining the therapeutically effective amount needed in specific embodiments of the present inventive without the need for undue experimentation.

As used herein, "resurfacing" of the skin for example and without limitation, refers to controlled injury to the skin cells. In certain embodiments, it may be intended that the inventive composition or formulations and/or non-thermal plasma impact the skin cells to disrupt the cells to promote cell turnover so that new healthier-looking skin emerges.

As used herein, "resurfacing" of the skin for example and without limitation in certain embodiments, it may be intended that the inventive compositions or formulation and/or non thermal plasma impact the structure of the skin enhancing transdermal absorption.

As used herein, "resurfacing" of the skin for example and without limitation in certain embodiments, it may be intended that these are methods and technique known in the art using lasers, light therapies, energy based treatments, chemical peels, needling and other processes to prevent and/or treat dermatological conditions such as wrinkled or sun-damaged skin, pigmentation issues, skin growths, scars, insufficient or excess hair, vascular conditions and skin elasticity and tone.

As used herein, "remodeling" of the skin for example and without limitation in certain embodiments, it may be intended that the inventive compositions or formulations and/or non-thermal plasma impact the structure of the skin enhancing transdermal absorption. It is understood that those of ordinary skilled in the art sometimes refer to "resurfacing" as "remodeling" and sometimes refer to "remodeling" as "rejuvenation".

As used herein, "remodeling" of the skin for example and without limitation in certain embodiments, it may be intended that the inventive compositions or formulations and/or non-thermal plasma impact the structure of the skin by improving the underlying components of the skin such as collagen, fibroblasts, melanin, proteins, keratinocytes, collagen chemical markers and so forth.

As used herein, "non-thermal plasma" refers for example and without limitation to plasma which is administered to a mammal or to a topical composition or formulation that is non-thermal. Non-thermal plasma is sometimes referred to by the technology used to generate it such as plasma needle, plasma jet, dielectric barrier discharge, etc., or it may be referred to a descriptive name such as atmospheric, atmospheric energy, ambient pressure, non-equilibrium or it may be referred to as "cold" plasma meaning that it is not thermal.

The inventive compositions or formulations may, in various exemplary, non-limiting embodiments be provided in forms suitable for topical administration and that result in the dermal delivery of a therapeutically effective amount, for example and without limitation the inventive composition or formulation may be provided as creams, gels, liquids, lotions, sprays, serums, emulsions, aerosols and combinations thereof, and may provide liposomes, lipid micro capsules, multi-lamellar vesicles, nanospheres, microsponges, transfersomes, or combinations thereof. In certain exemplary, non-limiting embodiments, the active agents may be encapsulated (including microencapsulated) in the inventive formulations, for example to be released when the encapsulating materials and techniques, including those with the encapsulated agent over time, are known in the art.

Other conventional cosmetic and/or pharmaceutical agents may be provided in the inventive compositions or formulations, so as long as they are physiologically acceptable and suitable for use in combination with the non-thermal plasma.

For example, the inventive delivery compositions or formulation may include physiologically compatible vehicle, such as water or organic compound, and derivatives, combinations and mixtures thereof. In certain desired embodiments, the inventive compositions or formulations may be oil-free vehicles. In certain desired embodiments, the inventive compositions or formulations may be substantially free of a skin penetration enhancer and/or an initiator compound.

For example, the inventive compositions or formulations may include emollients, skin conditioning agents, pH stabilizing agent(s), humectants, buffering agents, viscosity adjusting agents, preservatives, chelating agents, emulsifying agents, conditioning agents, thickening agents, wetting agents, antioxidants, UV stabilizers, UV radiation absorbers, sun-protecting ingredients, proteins, minerals and/or vitamins, steroids or stimulants, biologic ingredients, stem cells, fragrances, flavors and colorants.

The inventive compositions or formulations may also include mixtures and combinations and any of the above.

The inventive composition or formulation may also include or more active ingredients, for example and without limitation, agents for the prevention and/or treatment of one or more conditions, disorders and/or disease states.

It is understood that the therapeutically effective ingredient(s) or compound(s) may be present in the inventive formulation in any suitable amount.

As discussed herein, when administered, the inventive deliveries result in improvement in skin condition and an increased delivery of therapeutic ingredients with less side effect and/or injury to the skin. In certain desired, non-limiting embodiments, non-thermal plasma when administered to the skin results in skin remodeling and increased delivery of topically applied therapeutic ingredients.

The discussion herein and the following Examples set forth and illustrate various exemplary embodiments of the present invention, which are understood to be illustrative and non-limiting.

Example 1: Increase Delivery of Vitamin D to Maintain Good Health

A composition and/or formulation is prepared according to art-recognized techniques to have an amount of a therapeutically effective compound of ingredient to replace or increase ingredients made naturally in the body in order to achieve a particular therapeutic benefit, such as an increase in Vitamin D.

In such composition or formulation, the choice of vitamin D will depend on a number of factors, including the desired dose of the resulting formulation. For example, a lower dose may be desired to maintain vitamin D levels, while vitamin D insufficient or deficient mammals may require a composition or formulation with a higher therapeutic dose. In all cases, however, the inventive formulation provides a therapeutically effective amount of vitamin D that is administered topically with further enhancement of vitamin D delivery by non-thermal plasma application.

As with inventive treatments, these inventive treatments and/or preventative methods may be provided with different concentrations of vitamin D and other ingredients which are selected for each inventive composition or formulation, including the environmental and other conditions in which the inventive composition or formulation is intended to be used, as whether the inventive composition or formulation is intended to be re-applied after particular activities and/or specific period of time, and also taking into account specific characteristics of the mammal for whom it is intended that may impact absorption of vitamin D in such mammal.

As with the inventive treatments, these inventive treatments and/or preventative methods may be provided by a licensed healthcare professional and/or by a consumer based on the specific intended use of the resulting inventive treatments and/or preventative methods.

Accordingly, these inventive composition and/or formulations may be provided for use by a number of individuals engaged in varied activities and using these inventive compositions and/or formulations under varied conditions, while in all cases delivering an optimal amount of the therapeutic ingredient(s) in such individuals.

Example 2: Increase in Vitamin D to Prevent Disorders and Disease States

A composition or formulation is prepared according to the art-recognized techniques to have an amount of a therapeutically effective compound to treat and/or prevent a vitamin deficiency, such as a medical need to increase vitamin D.

In such composition or formulation, the choice of vitamin D will depend upon a number of factors, including the desired dose of the resulting formulation. For example maintaining, a vitamin D serum level of 30 ng/mL to 50 ng/mL reduces the risk of breast cancer by 30%-50%. Similar to oral formulations, individuals may require a composition or formulation at different therapeutic doses or for different courses of therapy or frequency. In all cases however the inventive formulation provides a therapeutically effective amount of vitamin D that is administered topically with further enhancement of vitamin D delivery by non-thermal plasma application.

As with inventive treatments, such conditions, disorders and/or diseases which may be prevented and/or treated using the inventive treatments and/or preventative methods include, for example and without limitation, dermatological conditions, disorders and diseases, bone-related disorders and diseases in diseases including osteopenia, osteomalacia, osteoporosis, vitamin and nutritional disorders, autoimmune disorders or diseases including multiple sclerosis, fibromyalgia, rheumatoid arthritis, Grave's disease and lupus, periodontal disorders and/or diseases; chronic pain; vascular disorders; seasonal affective disorder; cognitive impairment; depression; diabetes; chronic renal disease; cardiovascular and metabolic diseases and/or diseases; certain types of cancers including breast cancer, prostate cancer, colon cancer, pancreatic cancer and skin cancer.

As with treatments discussed above, in these inventive treatments and/or preventative methods, the choice of vitamin D will depend upon a number of factors, including the desired increase of the resulting treatments and/or preventative methods. For example, an individual with cystic fibrosis may require formulation with a higher dose and longer treatment period than an individual with osteoporosis to increase vitamin D delivery.

In all cases, however the inventive formulation provides a therapeutically effective amount of vitamin D that is administered topically with further enhancement of the vitamin D delivery by non-thermal plasma application.

Example 3: Increase in Vitamin D to Improve Skin Health

A composition or formulation is prepared according to the art-recognized techniques to have an amount of therapeutically effective compound or formulation to induct and deliver micronutrients into the skin, such as induction and delivery of vitamin D.

In such composition or formulation, the choice of vitamin D will depend on a number of factors, including the desired improvement to skin health. For example, vitamin D has a role in kerotinocyte production and induces peptides which have an antimicrobial and anti-endotoxin activity and as such plays a role in restructuring and anti-aging; and is also a major factor in cathelicidin regulation—dysfunction of cathelicidin is relevant to atopic dermatitis, rosacea and psoriasis. In all cases, however, the inventive formulations provides a therapeutically effective amount of vitamin D that is administered topically with further enhancement of vitamin D delivery by non-thermal plasma application.

As with inventive deliveries, these inventive deliveries may be provided with different concentrations of different forms of vitamin D and other ingredients which are selected for each inventive composition or formulation based on the specific intended use of the resulting inventive composition or formulation, including the environmental and other conditions in which the inventive composition or formulation is intended to be used, and whether the inventive composition or formulation is intended to be re-applied after particular activities and/or a specific period of time, and also taking into account specific characteristics of the mammal for whom it was intended that may impact the delivery of vitamin D in such mammal.

As with inventive treatments, such conditions, disorders and/or diseases which may be prevented and/or treated using the inventive treatments and preventative methods include, for example and without limitation, dermatological conditions, disorders and diseases consisting of acne, psoriasis, eczema, vitiligo, dermatitis, superficial lesions, actinic keratosis, seborrheic keratoses, lentigos, anti-aging including wrinkles, rhytides, pigmentation, redness, skin texture, tightness, scarring, pigmentation issues such as uneven pigmentation, melasma, pigmented lesions and tattoos, rebuilding collagen, elastin and overall skin rejuvenation; hair follicles and melanin stimulation or retardation of growth; fat and cellulite; vascular lesions such as birthmarks, facial veins and rosacea, spider and varicose veins.

As with treatments discussed above, in these inventive treatments and/or preventative methods, the choice of vitamin D will depend upon a number of factors, including the desired outcome of the resulting delivery. For example, activated vitamin D also known as calcitriol may be desired to improve psoriasis, while vitamin D3 may be desired to affect the skin's condition and anti-aging process.

In all cases, however, the inventive formulation provides a therapeutically effective amount of vitamin D that is administered topically with further enhancement of the vitamin D delivery by non-thermal plasma application.

As with inventive treatments, these inventive treatments and/or preventative methods may be provided with different concentrations of vitamin D and other ingredients which are selected for each inventive composition or formulation based on the specific intended use of the resulting inventive composition or formulation, including the environmental and other conditions in which the inventive composition or formulation is intended to be used, and whether the inventive composition or formulation is intended to be re-applied after particular activities and/or a specific period of time, and also taking into account specific characteristics of the mammal for whom it is intended that may impact delivery of vitamin D in such mammal.

Example 4: Delivery of the Topical Composition with at Least One Compound in a Pharmaceutical Carrier Enhanced by at Least One Application of Non-Thermal Plasma From the teachings provided herein, those of skill in the art will be able to make the inventive composition or formulation having at least one compound in a pharmaceutical carrier enhanced by at least one application of non-thermal plasma and test the safety and efficacy of such inventive composition or formulation with non-thermal plasma in animal models, for example and without limitation, animal models suited for intradermal and transdermal delivery, and using conventional in vivo and in vitro and/or pharmacokinetic analysis and techniques, as well as prepare such inventive compositions of formulations using ingredients to render them suitable for use by particular individuals, for use during particular Activities and/or for use when exposed to particular environmental conditions.

It is understood that the safety and efficacy of the formulations and compositions with non-thermal plasma application within the scope of the present invention may be determined on the basis of any skin concentration and non-thermal plasma concentration at which it is intended to be applied, and that in certain embodiments specific instructions may be provided, and/or the composition or the formulation or plasma application itself may be provided in a particular form, to ensure that a composition or formulation and/or plasma application is administered at the intended concentration (for example and without limitation, in certain embodiments of the composition or formulation of the present invention may be provided in a metered dose and/or non-thermal plasma may be provided in a pen-like handheld device, such as for use on certain parts of the body).

In certain non-limiting embodiments, vitamin D formulations that may be delivered to a patient according to the present invention in order to increase the patient's serum vitamin D level are those set forth in U.S. Pat. No. 8,470,304 (Ref. 3) and U.S. Pat. No. 8,709,387 (Ref. 4).

Example 5: Skin Rejuvenation Study

A 35-day study was conducted in three Sinclair minipigs. Minipigs were selected for the study due to their similarities to human skin and the immune system. They are widely used in general toxicity testing because their skin's thickness, permeability, pigmentation, allergic reaction and reactions to burning and distress is similar to human. The FDA notes that their immune system is better than rodents (Ref. 6).

Study Design.

Two Non-Thermal (NT) Plasma device treatment methods were assessed: (1) a Uniform Pulse; and (2) an Uneven Pulse. The Non-Thermal Plasma Device operate by non-thermal atmospheric pressure and did not require argon gas to operate. The Non-Thermal Plasma Device Treatment was applied above the skin of the pigs weekly (6 treatments over 35 days) according to the treatment time and pulse parameters described below. As micronutrients help to keep the skin healthy, in addition to the Non-Thermal Plasma device treatment, a therapeutic composition of vitamin D in a pharmaceutical Carrier was applied daily (5 g) to all three pigs. A 2 mm punch biopsy was collected on Day 0, Day 14 and Day 35 to assess efficacy and safety. An investigator-assessed tolerability ordinal scale: (0=none; 1=minimal; 2=mild; 3=moderate; and 4=severe) was used to measure tolerability defined as erythema (redness), pigment changes (creation of melanin deposits, e.g., brown spots; or color changes, e.g., white spots) and demarcation damages (holes in the skin, bruising or blisters or ulcers or irritation or visible unfavorable skin reaction). Photo imaging was also used in the evaluation.

TABLE 1

Non-Thermal Plasma Treatment Parameters.

| Treatment | Pig 1 NT Plasma + Carrier Cream | Pig A: NT Plasma + Carrier Cream | Pig X: No Plasma (Carrier Cream only) |
|---|---|---|---|
| Power Supply | Uniform Pulse "nanosecond" | Uneven Pulse "microsecond" | N/A |
| Voltage | 31 kV | 20 kV | N/A |
| Distance from skin | 1-2 mm | 1-2 mm | N/A |
| Treatment Time per quadrant | ~30 seconds | ~30-45 seconds | N/A |
| Frequency of Pulse | 1,000 Hz | 1,000 Hz | N/A |

Voltage, frequency of pulse and treatment time may vary based on the type and condition of skin being treated (e.g., fine lines, rhytides as compared to more photo damaged skin, blemished skin as compared to non-blemished skin, sensitive skin compared to normal skin, part of skin being treated (e.g., face, hands, legs), amount of skin being treated (face as compared to face, neck and chest), etc.

A. Skin Rejuvenation/Restructuring Primary Efficacy Endpoints.

Skin Rejuvenation/Restructuring primary efficacy endpoints were defined as increases in fibroblast proliferation or increase in collagen (collagen I, or collagen III or hydroxyproline) or increases in skin thickness or elastin or a reduction in e-cadherin as measured by Day 35 increases compared to Day 0 (baseline).

TABLE 2

Results: Skin Restructuring/Rejuvenation Primary Efficacy Endpoints (Day 35 mean increases compared to Day 0 mean baseline).

| | Pig 1: NT Plasma Uniform Pulse + Carrier Cream | | Pig A: NT Plasma Uneven Pulse + Carrier Cream | | Pig X: No Plasma (Carrier Cream only) | |
|---|---|---|---|---|---|---|
| Rejuvenation Endpoints | Day 0 | Day 35 Mean % Increase | Day 0 | Day 35 Mean % Increase | Day 0 | Day 35 Mean % Increase |
| Fibroblasts | 54.7 | +18.9% | 35.7 | +96.3% | 80.7 | −56.2% |
| Skin Thickness | 1.1 | +2.9% | 1.3 | −2.9% | 1.1 | +2.9% |
| Elastin | | No change | | No change | | No change |
| Collagen (Trichrome) | | No change | | No change | | No change |
| E-Cadherin stain | | Decrease | | Decrease | | Decrease |

The primary skin rejuvenation endpoints were met. The Non-thermal (NT) Plasma Uniform Pulse device combined with the Carrier Cream resulted in mean increases in fibroblast production (+18.9%) day 35 compared to baseline mean day 0 (54.7) and a mean increase of 2.9% in epidermal thickness day 35 compared to day 0 (1.1). The NT Plasma Uneven Pulse device in combination with the Carrier Cream resulted in mean increases in fibroblasts (+96.3%) compared to baseline mean day 0 (35.7) with a reduction in epidermal thickness (−2.9%). Epidermal thickness was measured using an Olympus graticule (linear micrometer, WH10x/22) ocular. Skin rejuvenation/restructuring is evidenced by the increase in fibroblasts and skin thickness.

The six plasma treatment applications using both the NT Plasma Uniform Pulse device combined with the Carrier Cream and the NT Plasma Uneven Pulse device in combination with the Carrier Cream did not yet evidence changes to elastin or collagen. Collagen was assessed using the Trichrome stain as the chemical collagen marker hydroxyproline was not available at the time of the study. Similar to laser restructuring therapies, the collagen remodeling response is delayed typically to 3 and 12 months after treatment (Ref. 7). Improved collagen from topical retinoids has shown also to require six months or longer treatment (Ref. 8). Longer-term studies (>35 days) are needed to assess effects on improved elastin and collagen.

A decrease in e-cadherin stain in superficial layers of the epidermis was evidenced in all three applications (the NT Plasma Uniform Pulse device combined with the Carrier Cream, the NT Plasma Uneven Pulse device combined with the Carrier Cream and the Carrier Cream alone indicating a disruption or alteration of cell adhesion (skin restructuring)

which demonstrates enhanced skin permeability resulting in an increased absorption of topical compounds.

Additional histology was performed to assess tissue cell and skin improvement.

TABLE 3

Results: Skin Rejuvenation/Restructuring Secondary Analysis (Day 35 mean increase as compared to Day 0 mean baseline).

| | Pig 1: NT Plasma Uniform Pulse + Carrier Cream | | Pig A: NT Plasma Uneven Pulse + Carrier Cream | | Pig X: No Plasma (Carrier Cream only) | |
|---|---|---|---|---|---|---|
| Skin Rejuvenation | Day 0 | Day 35 Mean % Increase | Day 0 | Day 35 Mean % Increase | Day 0 | Day 35 Mean % Increase |
| Squamous cells | 130.7 | +48.5% | 85.7 | +113.6% | 260.7 | −36.1% |
| Melanocytes | | No change | | No change | | No change |
| CD163 cells | 13.0 | +43.6 | 16.7 | −54.0 | 36.0 | −79.6 |

Both the NT Plasma Uniform Pulse device combined with the Carrier Cream and the NT Plasma Uneven Pulse device combined with the Carrier Cream showed improvements in squamous cells. The NT Plasma Uniform Pulse in combination with the Carrier Cream resulted in a mean increase in squamous cell production day 35 (+48.5%) compared to mean baseline day 0 (130.7) and the NT Plasma Uneven Pulse device in combination with the Carrier Cream demonstrated a mean increase of 113.6% compared to baseline mean day 0 (85.7) evidencing cell restructuring and turnover. Increased squamous cell production assists in the production of the protective protein keratin. When the skin is traumatized, an increase in melanocytes can be seen. There was no change in melanocyte production. Only the NT Plasma Uniform Pulse device in combination with the Carrier Cream demonstrated a positive mean increase in CD163 (monocytes/macrophages/dendritic cells) day 35 mean (+43.6%) compared to mean baseline day 0 (16.7).

B. Skin Rejuvenation/Restructuring Safety and Tolerability.

Skin safety and tolerability were measured to assess the absence of cutaneous side effects. Safety was defined as erythema (redness), pigmentation changes (creation of melanin deposits, e.g., brown spots; or color changes, e.g., white spots) and demarcation damage (holes in the skin, bruises or blisters or ulcers or irritation or visible unfavorable skin reaction). Safety and tolerability were assessed using biopsied histology on Day 0, Day 14 and Day 35 and an investigator-assessed skin irritation and other cutaneous side effects after each treatment using an ordinal damage scale: 0=none, 1=minimal, 2=mild, 3=moderate and 4=severe. Skin hydration was assessed by Transepidermal Water Loss (TEWL) testing and a colorimeter test was used to assess melanin changes.

As can be seen from the tables below there was no skin damage or skin toxicities resulting from any of the NT Plasma device treatments in combination with the Carrier Cream and no skin damage or toxicity in Pig X with the Carrier Cream alone. Combination NT Plasma device treatments and the Carrier Cream alone did not affect TEWL (water loss/hydration) from the skin and there was no erythema, undesirable pigment changes or skin damage.

TABLE 4

Results: Skin Rejuvenation/Restructuring Safety and Tolerability: Erythema, Pigment and Demarcation (Ordinal Damage Scale: 0 = None; 1 = Minimal; 2 = Mild; 3 = Moderate; 4 = Severe).

| | PIG1: NT Plasma Uniform Pulse + Carrier | | PIG A: NT Plasma Uneven Pulse + Carrier | | PIG X: No Plasma (Carrier Only) | |
|---|---|---|---|---|---|---|
| | Day 0 | Day 35 | Day 0 | Day 35 | Day 0 | Day 35 |
| Erythema | 0 | 0 | 0 | 0 | 0 | 0 |
| Pigment Change | 0 | 0 | 0 | 0 | 0 | 0 |
| Demarcation Damage | 0 | 0 | 0 | 0 | 0 | 0 |
| TEWL | | No change | | No change | | No change |
| Colorimeter | | No change | | No change | | No change |

C. Skin Rejuvenation/Restructuring Safety Histology Analysis.

Histology analysis was conducted by biopsy to assess the absence of damage to the epidermis characterized by separation of the keratinized and non-keratinized layers of the epidermis, vacuolar degeneration (damage to the basal layer with intercellular edema and vacuoles), dermal connective tissue damage (disruption of the epidermal-dermal junction) and vascular damage.

A 2 mm punch biopsy was collected on Day 0, Day 14, and Day 35. Histological stains of tissues was performed with the following stains.

Hematoxylin and Eosin (H&E) stains to detect any cell mutations, morphological changes, presence of epidermal and dermal edema, necrosis and apoptosis of cells, inflammatory cells, vascular congestions/dilation and erythema. No changes were detected from baseline in any treatment.

E-Cadherin stain to assess cell to cell adhesion. A loss or decrease in stain intensity indicates a disruption or alteration of cell adhesion which has been shown to increase skin permeability. As indicated previously, stain intensity was decreased in all treatments indicating cell disruption and increased skin permeability.

Trichrome stain to evidence changes in connective tissue fibers and fibrosis (scarring). No changes were detected from baseline in any treatment.

Periodic Acid Schiff (PAS) stain to evaluate the integrity of the epidermal basement membrane. Interruptions, thinning or thickening of the basement membrane can be detected from this stain. No changes were detected from baseline in any treatment.

Mart-1 stain to detect melanocytic lesions). When skin is traumatized, a proliferation of melanocytes is often detected. No changes were detected from baseline in any treatment. CD163 stain to assess for abnormal tissue and determine the number of CD163 positive cells (monocytes/macrophages/dendritic cells. No abnormal tissues from baseline were detected in ant treatment.

There was an absence of toxicity to the skin architecture and cellular composition and no significant differences were found comparing mean Day 35 to Day 0 (mean baseline).

Summary of Non-Thermal Plasma Rejuvenation/Restructuring.

The Non-Thermal Plasma Device applications in combination with the Carrier Cream, both NT Plasma Uniform Pulse Device treatments in combination with the Carrier Cream and NT Plasma Uneven Pulse treatments in combination with the Carrier Cream resulted in Skin Rejuvenation/Skin Restructuring. Primary and secondary clinical end-points demonstrated increases in fibroblasts (mean increase +18.9% and, +96.3% respectively day 35 compared to baseline day 0 and improvements in squamous cells (mean increase +48.5% and +113.6% compared to baseline day 0. Increase in epidermal thickness was evidenced only in the Uniform Plasma Pulse device combined with the Carrier System.

Both Uniform Plasma and Uneven Plasma Pulse devices in combination with the Carrier System demonstrated an absence of skin damage (holes in the skin, bruising or blisters or ulcers or irritation or visible unfavorable skin reactions), an absence of erythema (redness) and no undesirable pigmentation changes or loss of skin hydration (TEWL). Tolerability assessments demonstrated no skin redness irritation. Histology demonstrated no change in toxicity to skin architecture and cellular composition following single application of Non-Thermal Plasma applications (both Uniform Pulses and Uneven Pulses) in combination with the Carrier Cream or following multiple treatment applications. Also, there were no changes in toxicity, skin damage, undesirable pigmentation changes or loss of skin hydration in the Carrier Cream only treated pig (Pig X).

Example 6: Non-Thermal Plasma Tattoo Study

A five-week pilot study was conducted in 2 minipigs to assess the safety of tattoo removal using Non-thermal Plasma nanosecond uniform pulse and Non-thermal Plasma microsecond uneven pulse. Four treatment areas were tested on each pig for high, medium and lose dose plasma and one control area (no plasma). NT Plasma was applied to the treatment areas weekly with the parameters set forth in Table 5.

TABLE 5

Tattoo Removal Treatment Parameters.

| | Pig 1 | Pig A |
|---|---|---|
| Power Supply | Nanosecond Pulsed | Microsecond Pulsed |
| Voltage | 31 kV | 20 kV |
| Treatment Time | 10 seconds | 10 seconds |
| Distance from skin | 2 mm | 2 mm |
| Frequency of Pulses (D) | 1000 Hz | 1000 Hz |
| For Tattoo Removal: | | |
| Low (L) | 100 Hz | 50 Hz |
| Medium (M) | 550 Hz | 860 Hz |
| High (H) | 1000 Hz | 1000 Hz |

Safety/tolerability was assessed using an investigator-assessed tolerability ordinal scale: (0=none; 1=minimal; 2=mild; 3=moderate; 4=severe) to measure erythema (redness), pigment changes (creation of melanin deposits, e.g., brown spots or white spots) and demarcation damages (holes in the skin, bruising or blisters or ulcers or irritation or visible unfavorable skin reactions). Safety/tolerability study demonstrated both regiments of NT Plasma nanosecond and microsecond demonstrated no safety issues.

TABLE 6

Tattoo Removal Skin/Skin Cell Tolerability Assessment (Scale: 0 = None; 1 = Minimal; 2 = Mild; 3 = Moderate; 4 = Severe).

| Day | | Pig 1 L | Pig 1 M | Pig 1 H | Pig 1 C | Pig A L | Pig A M | Pig A H | Pig A C |
|---|---|---|---|---|---|---|---|---|---|
| 0 | Erythema | 0 | 0 | 0 | 0 | 0 | 0 | 0 | 0 |
| 0 | Pigment Change | 0 | 0 | 0 | 0 | 0 | 0 | 0 | 0 |
| 0 | Demarcation Damage | 0 | 0 | 0 | 0 | 0 | 0 | 0 | 0 |
| 7 | Erythema | 0 | 0 | 0 | 0 | 0 | 0 | 0 | 0 |
| 7 | Pigment Change | 0 | 0 | 0 | 0 | 0 | 0 | 0 | 0 |
| 7 | Demarcation Damage | 0 | 0 | 0 | 0 | 0 | 0 | 0 | 0 |
| 14 | Erythema | 0 | 0 | 0 | 0 | 0 | 0 | 0 | 0 |
| 14 | Pigment Change | 0 | 0 | 0 | 0 | 0 | 0 | 0 | 0 |
| 14 | Demarcation Damage | 0 | 0 | 0 | 0 | 0 | 0 | 0 | 0 |
| 21 | Erythema | 0 | 0 | 0 | 0 | 0 | 0 | 0 | 0 |
| 21 | Pigment Change | 0 | 0 | 0 | 0 | 0 | 0 | 0 | 0 |
| 21 | Demarcation Damage | 0 | 0 | 0 | 0 | 0 | 0 | 0 | 0 |
| 28 | Erythema | 0 | 0 | 0 | 0 | 0 | 0 | 0 | 0 |
| 28 | Pigment Change | 0 | 0 | 0 | 0 | 0 | 0 | 0 | 0 |
| 28 | Demarcation Damage | 0 | 0 | 0 | 0 | 0 | 0 | 0 | 0 |
| 35 | Erythema | 0 | 0 | 0 | 0 | 0 | 0 | 0 | 0 |
| 35 | Pigment Change | 0 | 0 | 0 | 0 | 0 | 0 | 0 | 0 |
| 35 | Demarcation Damage | 0 | 0 | 0 | 0 | 0 | 0 | 0 | 0 |

Example 7: Vitamin D Transdermal Induction Therapy Study

A 6-week study was conducted on three minipigs to assess the safety and efficacy of a novel non-Thermal Plasma device to induce topical ingredients for a therapeutic effect of a composition in a pharmaceutical Carrier to improve a nutrient deficiency. The Non-Thermal Plasma device treatment was applied weekly over 5 weeks to vitamin D deficient minipigs (vitamin D 25(OH)D<30 ng/mL) to enhance induction and therapeutic increases of vitamin D3 (cholecalciferol—384.6 Daltons). A therapeutic cream composition of a fixed dose of vitamin D3 in a clinically proven Carrier not requiring the use of chemical enhancers was applied daily (5 g) to all three pigs. Two different Non-Thermal Plasma device pulses, Uniform and Uneven were tested in single induction applications (Day 0) and five repeat induction applications on weeks 1, 2, 3, 4 and 5. Vitamin D levels were assessed on Day 0, Day 35 and Day 42 by 25(OH)D serum levels. The induction therapy treatment parameters are reported in the table below.

TABLE 7

| Induction Therapy Treatment Parameters. | | | |
|---|---|---|---|
| Treatments | Pig 1 NT Plasma + Carrier | Pig A: NT Plasma + Carrier | Pig X: No Plasma (Carrier only) |
| Daily Vitamin D cream in Carrier | 5 grams: fixed dose | 5 grams: fixed dose | 5 grams: fixed dose |
| Power Supply | Uniform Pulse "nanosecond" | Uneven Pulse "microsecond" | N/A |
| Voltage | 31 kV | 20 kV | N/A |
| Distance from skin | 1-2 mm | 1-2 mm | N/A |
| Treatment Time per quadrant treated | ~30 seconds | ~30-45 seconds | N/A |
| Frequency of Pulse | 1,000 Hz | 1,000 Hz | N/A |

Voltage, frequency of pulse and treatment time may vary based on the condition of skin being treated (e.g., damaged versus normal skin), part of skin being treated (e.g., scalp, body, face), surface area of skin being treated (e.g., amount of skin surface treated), and size of the molecules being introduced (e.g., large molecules compared to small molecules.)

Study Design.

A baseline 25(OH)D vitamin D3 serum sample was collected on Day 0 for all three pigs followed by a 25(OH)D vitamin D3 serum collection on Day 35 and Day 42. Day 0, 35 and 42 were batch processed by an outside laboratory at the end of the study. The vitamin D3 cream composition was applied daily (5 g) to all three pigs. A single induction of the Non-Thermal Plasma device was applied to Pig 1 (Uniform Pulse) and Pig A (Uneven Pulse) on Days 0, 7, 14, 21, 28 and 35. Application of the therapeutic dose of Vitamin D3 (5 g) was applied daily for 35 days. A 2 min punch biopsy was collected on Day 0, Day 14 and Day 35 to assess safety and tolerability. In addition to a biopsied histological evaluation, an investigator-assessed tolerability ordinal scale: (0=none, 1=minimal, 2=mild, 3=moderate and 4=severe) was used to measure erythema, pigment changes and demarcation damages, specifically holes in the skin, bruising or blisters or ulcers or visible unfavorable skin reaction. Photo imaging was also used in the assessment.

A. Transdermal Induction Therapy Efficacy Endpoints.

Day 42 Transdermal Induction Therapy efficacy endpoints of Vitamin D 25(OH)D blood serum levels Day were compared to Day 0. Day 42 increases compared to Baseline (Day 0) are in Table 8.

TABLE 8

| Results: Transdermal Induction Therapy Efficacy Vitamin D Endpoints (Day 42 increases compared to Baseline Day 0). | | | |
|---|---|---|---|
| | Pig X | Pig 1 | Pig A |
| Vitamin D Serum Level | No Plasma (Carrier only) | NT Plasma Device Uniform Pulse + Carrier | NT Plasma Device Uneven Pulse + Carrier |
| Day 0 | 52 nmol/L (16.4 ng/mL) | 44 nmol/L (13.8 ng/mL) | 37 nmol/L (11.6 ng/mLP) |
| Day 42 increase | +436.5% | 568.2% | 416.2% |

Transdermal Induction therapy of vitamin D nutrient demonstrated increase in vitamin. D (25(OHD) serum levels) as compared to baseline Day 0 (nutrient deficiency) was achieved on day 42 in the pharmaceutical Carrier alone and in the combination treatment of the Carrier and the NT Plasma Uniform and Uneven Pulse devices. An increase was demonstrated on Day 35 compared to baseline Day 0 in all three treatments. Baseline Vitamin D serum levels 25(OH)D evidenced vitamin D deficiency (25(OH)D<30 ng/mL) in all three minipigs. The NT Plasma Uniform Pulse Device enhanced delivery by 131.7% as compared to the fixed dose Carrier alone. Pig X (Fixed Dose Carrier alone) baseline vitamin D serum level was 15.4% higher than Pig 1 (NT Plasma Uniform Pulse plus Carrier) and 28.8% higher than Pig A (NT Plasma Uneven Pulse Device plus Carrier). Adjusting the baseline NT Plasma Uniform Pulse Device and Carrier combined might result in further increased of the NT Plasma Devices combined with the Carrier compared to the Carrier alone.

B. Skin Improvement.

Skin rejuvenation endpoints were measured by an increase in histological skin markers such as fibroblast proliferation or collagen or increases in epidermal thickness, elastin or decreases in e-Cadherin measuring the change from Day 35 compared to Day 0 (Baseline). Results are indicated in Table 9.

TABLE 9

| Results: Transdermal Induction Therapy Efficacy Skin Improvement Endpoints. | | | | | | |
|---|---|---|---|---|---|---|
| | Pig X: No Plasma (Delivery Carrier only) | | Pig 1: NT Plasma Uniform Pulse + Carrier | | Pig A: NT Plasma Uneven Pulse + Carrier | |
| Skin Improvement | Day 0 | Day 35% Inc. | Day 0 | Day 35% Inc. | Day 0 | Day 35% Inc. |
| Fibroblasts | 80.7 | −56.2% | 54.7 | 18.9% | 35.7 | 96.5% |
| Epidermal Thickness | 1.1 | +2.9% | 1.1 | +2.9% | 1.1 | −2.9% |
| Elastin | No change | No change | No change | No change | No change | No change |
| Collagen | No change | No change | No change | No change | No change | No change |
| E-Cadherin | | Decreased | | Decreased | | Decreased |

Study endpoints were achieved evidencing fibroblast production was numerically significantly enhanced with the NT Plasma Uniform Pulse device in combination with the pharmaceutical Carrier and the NT Plasma Uneven Pulse device in combination with the pharmaceutical Carrier compared to the pharmaceutical Carrier alone. There were no meaningful changes in epidermal thickness of the NT Plasma Devices in combination with the Carrier compared to the pharmaceutical Carrier alone and no histological changes to elastin and collagen compared to the pharmaceutical Carrier alone or baseline. Collagen was assessed using the Trichrome stain.

C. Transdermal Induction Therapy E-Cadherin.

E-Cadherin stains were analyzed to evidence skin remodeling via the creation of a opening gap in the epidermal tissues to enable the induction of the therapeutic vitamin D in a pharmaceutical Carrier alone and in combination with the NT Plasma devices. A decrease in e-cadherin stain was evidenced in the superficial layers of the epidermis in the pharmaceutical Carrier alone, the NT Plasma Uniform Pulse device and the NT Plasma Uneven Pulse device indicating a disruption or alteration of cell adhesion (skin restructuring). The histological stain demonstrated a decrease (disruption of the epidermal tissues). Such disruption could enable enhanced permeability in the skin resulting in an increased absorption of topical compounds. The resultant therapeutic increase in vitamin D serum levels on day 42 in Pig X demonstrated a numerically significant increase (+436.5%) that was further enhanced with the NT Plasma Uniform Pulse device (+131.7%) before adjusting for vitamin D3 baseline levels. Adjusting for baseline vitamin D3 to the higher baseline serum level of Pig X Carrier alone might results in higher increases of the NT Plasma treatments combined with the pharmaceutical Carrier as compared to the pharmaceutical Carrier alone.

Additional histology was performed to assess tissue cell and skin improvement as reported in Table 10.

TABLE 10

Results: Transdermal Induction Therapy Efficacy Endpoints Other Analysis.

| Secondary Analysis | Pig X: No Plasma (Carrier only) | | Pig 1: NT Plasma Uniform Pulse + Carrier | | Pig A: NT Plasma Uneven Pulse + Carrier | |
|---|---|---|---|---|---|---|
| Skin Improvement | Day 0 | Day 35% Inc. | Day 0 | Day 35% Inc. | Day 0 | Day 35% Inc. |
| Ki-67 stain | 170.7 | −40.8% | 92.7 | 39.7% | 60.7 | 108.5% |
| Melanocytes | No change | No change | No change | No change | No change | No change |
| CD163 | 36.0 | −79.6% | 13.0 | +43.6% | 16.7 | −54.0 |

The Ki-67 protein is tightly regulated and depends on the proliferative status of a cell. It is present in the nuclei of proliferating cells but absent in resting cells. Since transformation of malignant cells is frequently associated with high cell proliferation and since proliferation is tightly associated with the Ki-67 protein labeling index, this antigen may represent a potential target for cancer therapy (Kausch, 2003; Ref. 9). Vitamin D has been reported to reduce Ki-67 in cancer patients (prostrate and breast). The Ki-67 stain for skin analysis also evaluates the production of cells (fibroblasts, squamous/keratinocyte cells). Both the NT Plasma Uniform Pulse device in combination with the Carrier and the NT Plasma Uneven Pulse device in combination with the Carrier demonstrated improvements in squamous and fibroblasts cells. The NT Plasma Uniform Pulse device in combination with the Carrier resulted in a mean increase in squamous cell production day 35 (+48.5%) compared to mean baseline day 0 (130.7). The NT Plasma Uneven Pulse device in combination with the Carrier had a mean increase of 113.6% compared to baseline mean day 0 (85.7) evidencing cell restructuring and cell turnover from both. Increased squamous cell production assist in the production of the protective protein keratin. Both NT Plasma device treatments were enhanced compared to Carrier alone. When the skin is traumatized, an increase in melanocytes can be seen. There was no change in melanocyte production for any treatment. Only the NT Plasma Uniform Pulse device in combination with the Carrier demonstrated a positive mean increase in CD163 (monocytes/macrophages/dendritic cells) day 35 mean (43.6%) compared to mean baseline day 0 (16.7).

D. Transdermal Induction Therapy Safety and Tolerability.

Serum Vitamin D levels were normalized in the three vitamin D deficient minipigs for all three treatments after 35 days treatments without any adverse events.

Skin safety and tolerability were measured to assess the absence of cutaneous side effects (erythema, pigmentation changes and demarcation damage, specifically holes in the skin, bruised or blisters or ulcers or visible unfavorable skin reaction.) and skin irritation. Assessments were made using an ordinal scale: 0=none; 1=minimal; 2=mild; 3=moderate; 4=severe). Skin hydration was assessed by Transepidermal Water Loss (TEWL) testing and a colorimeter test was used to assess melanin changes. As can be seen from the tables below there was no immediate skin toxicity of the Non-Thermal Plasma treatments or the Carrier alone. Non-Thermal Plasma treatments in combination with the Carrier and the Vitamin D Carrier alone did not affect water loss (hydration) from the skin.

TABLE 11

Results: Induction Therapy Safety and Tolerability: Erythema, Pigment and Demarcation (holes in the skin, bruises, or blisters or ulcers or visible unfavorable skin reaction.) measure by Investigator- Assessed Ordinal Scale.

| | PIG 1: NT Plasma Uniform Pulse + Carrier | | PIG A: NT Plasma Uneven Pulse + Carrier | | PIG X: No Plasma (Carrier alone) | |
|---|---|---|---|---|---|---|
| | Day 0 | Day 35 | Day 0 | Day 35 | Day 0 | Day 35 |
| Erythema | 0 | 0 | 0 | 0 | 0 | 0 |
| Pigment Change | 0 | 0 | 0 | 0 | 0 | 0 |
| Demarcation Damage | 0 | 0 | 0 | 0 | 0 | 0 |
| Infection | 0 | 0 | 0 | 0 | 0 | 0 |
| TEWL | | No change | | No change | | No change |
| Colorimeter | | No change | | No change | | No change |

E. Transdermal Induction Therapy Tolerability Secondary Analysis.

Secondary safety analysis was conducted by biopsy to assess the absence of damaging changes to the epidermis characterized by separation of the keratinized and non-keratinized layers of the epidermis, vacuolar degeneration (damage to the basal layer with intercellular edema and vacuoles), dermal connective tissue damage (disruption of the epidermal-dermal junction) and vascular damage.

A 2 mm punch biopsy was collected on Day 0, Day 14 and Day 35. Histological stains of tissues were performed including Hematoxylin/Eosin (to detect any cell mutations and morphological changes), E-Cadherin (to detect any loss or abnormalities), Trichrome (to evidence changes in connective tissue fibers), Periodic Acid Schiff (to evaluate epidermal basement membrane, blood vessels and the presence of fungal organisms), Mart-1 (to detect melanocytic lesions) and CD163 (to assess for abnormal tissue). As can be, seen from the table below, there was an absence of toxicity to the skin architecture and cellular composition and no significant differences were found from baseline (Day 0) and Day 35 in the Non-Thermal Plasma treatments and the Delivery carrier.

TABLE 12

Results: Transdermal Induction Therapy Tolerability Secondary Analysis: Histology Assessment.

| Stain | Purpose | Result |
|---|---|---|
| Hematoxylin and Eosin (H&E) | Detect cell mutations, morphological changes, presence of epidermal and dermal edema, necrosis and apoptosis of cells, inflammatory cells, vascular congestions/dilation and erythema. | No changes were detected from baseline for any treatment. |
| E-Cadherin | Assess cell to cell adhesion | A loss or decrease in stain intensity indicates a disruption or alteration of cell adhesion which has been shown to increase skin permeability. Stain intensity was decreased in all treatments indicating cell disruption and increased skin permeability. |
| Collagen Trichrome | Evidence changes in connective tissue fibers and fibrosis (scarring). | No changes were detected from baseline for any treatment. |
| Periodic Acid Schiff (PAS) | Evaluate the integrity of the epidermal basement membrane. Interruptions, thinning or thickening of the basement membrane can be detected from this stain | No changes were detected from baseline for any treatment. |
| Mart-1 | Detect melanocytic lesions). | No changes were detected from baseline for any treatment. |
| CD163 | Assess for abnormal tissue and determine the number of CD163 positive cells (monocytes/macrophages/ dendritic cells. | No abnormal tissues from baseline were detected for any treatment. |

There was an absence of toxicity to the skin architecture and cellular composition and no significant differences were found comparing mean Day 35 to Day 0 (mean baseline) for all treatments.

Summary Transdermal Induction Therapy.

Non-Thermal Plasma Uniform Pulse device in combination with Carrier delivery increased Vitamin D 25(OH)D serum levels by 131% as compared to the Carrier delivery alone on Day 42. Similar to previous studies, the vitamin D fixed dose Carrier demonstrated significant numeric increases compared to baseline (Day 35 +742%, Day 42 +437%) and normalized vitamin D levels following 35 days daily application. Further transdermal induction studies of the technologies alone and in combination will be conducted on larger sized molecules.

The clinical endpoints for skin improvement as evidenced by increased fibroblasts compared to baseline (NT Plasma Uniform Pulse device in combination with the Carrier +18.9%; NT Plasma Uneven Pulse device in combination with the Carrier +96.3%) were achieved in the absence of skin toxicity and damage (holes in the skin, bruising or blisters or ulcers or irritation or visible unfavorable skin reaction). The Non-Thermal Plasma device combined with the vitamin D pharmaceutical Carrier did not result in erythema or undesirable pigmentation changes and skin hydration was maintained as evidenced by TEWL. Tolerability assessments demonstrated no irritation or infection. Safety histology demonstrated no change in toxicity to skin architecture and cellular composition following single application of Non-Thermal Plasma applications in combination with the Vitamin D delivery Carrier for either NT Plasma Uniform Pulses or NT Plasma Uneven Pulses and no change in skin damage following multiple applications and plasma treatments. There were no adverse events with the Vitamin D Carrier alone.

Once given the above disclosure, and many other features, modifications and improvements will become apparent to the skilled artisan. Such features, modifications, and improvements are therefore considered to be part of this invention, without limitation imposed by the example embodiments described herein. Moreover any word, term, phrase, feature, example, embodiment, or part or combination thereof, as used to describe or exemplify embodiments herein, unless unequivocally set forth as expressly as expressed uniquely defined or otherwise unequivocally set forth is limiting, is not intended to impart a narrowing scope to the invention in contravention of the ordinary meaning of the claim terms by which the scope of the patent property rights shall otherwise be determined. All references discussed and disclosed herein and thereby incorporated by reference in their entirety.

REFERENCES

1. U.S. Pat. No. 4,911,928 (Wallach).
2. U.S. Pat. No. 5,629,021 (Wright).
3. U.S. Pat. No. 8,470,304 (Gardner).
4. U.S. Pat. No. 8,709,387 (Gardner).
5. U.S. Pat. No. 8,725,248 (Gustol).
6. *Animal Models in Toxicology* (2006) *Second Edition*, edited by Shayne C. Gad. (https://books.google.com/ books?id=RnoIrYxR264C&pg=PA733&lpg=PA733&dq=sinclair+mini+pigs+and+human+skin&source=bl&ots=OMV8gC5vjo&sig=IQSSAy2a1cPa4h0D8NTiTeMutO&h1=en&sa=X&ved=0CB0Q6AEwADgKahUKEwjIxMrdjtTHAhXFbj4KHQVPB9Q#v=onepage&q=sinclair%20mini%20pigs%20and%20human%20skin&f=false).

7. Ganceviciene R, Liakou A I, Theodoridis A, Makrantonaki E, Zouboulis C C. Skin anti-aging strategies. *Dermato-endocrinology*. (2012) 4(3):308-319 (doi: 10.4161/derm.22804).
8. Mukherjee S, Date A, Patravale V, Korting H C, Roeder A, Weindl G. Retinoids in the treatment of skin aging: an overview of clinical efficacy and safety. *Clinical Interventions in Aging*. (2006) 1(4):327-348.
9. Kausch, I. et al., "Antisense treatment against Ki-67 mRNA inhibits proliferation and tumor growth in vitro and in vivo." *Int. J. Cancer* (2003) 105(5):710-6.

What is claimed is:

1. A method of treating and/or preventing a medical condition in a patient in need thereof, said method comprising (a) the application of non-thermal plasma to the skin of said patient, wherein said non-thermal plasma application results in the resurfacing, rejuvenation or the remodeling of the skin of said patient; and (b) topical administration of a therapeutic composition to the skin of said patient, said therapeutic composition comprising (i) an active ingredient present in said therapeutic composition in a therapeutically effective amount; and (ii) a pharmaceutical carrier effective for topical administration of said active ingredient, wherein said non-thermal plasma application enhances delivery and/or induction of said therapeutic composition to the skin of said patient.

2. A method of treating and/or preventing a medical condition in a patient in need thereof according to claim 1, wherein said non-thermal plasma is administered to said patient by high voltage energy positioned between an electrode and said patient's skin and wherein said electrode is positioned on or above said patient's skin.

3. A method of treating and/or preventing a medical condition in a patient in need thereof according to claim 1, wherein said application of said non-thermal plasma disrupts said patient's skin without creating holes or thermal damage to the outer skin and wherein said application of said non-thermal plasma improves the health of said patient's skin.

4. A method of treating and/or preventing a medical condition in a patient in need thereof according to claim 1, wherein said therapeutic composition is topically applied to said patient's skin in a single application or in multiple applications.

5. A method of treating and/or preventing a medical condition in a patient in need thereof according to claim 4, wherein said active ingredient is encapsulated.

6. A method of treating and/or preventing a medical condition in a patient in need thereof according to claim 5, wherein said active ingredient is present in said patient's blood serum in an increased amount following said topical administration of said therapeutic composition.

7. A method of treating and/or preventing a medical condition in a patient in need thereof according to claim 5, wherein said therapeutically effective amount of said active ingredient is an amount sufficient to compensate for a reduction in said patient's natural production of said active ingredient or an insufficiency in the presence of said active ingredient in said patient and increases the amount of said active ingredient in said patient.

8. A method of treating and/or preventing a medical condition in a patient in need thereof according to claim 5, wherein said active ingredient is selected from the group consisting of cosmetic ingredients, pharmaceutical ingredients, nutritional ingredients, minerals, vitamins, steroids, stimulants, stem cells, biologic ingredients, combinations, active forms and metabolites thereof and wherein said therapeutic composition is in the form of a cream, gel, liquid, lotion, solution, spray, emulsion, serum, aerosol, foam, or a combination thereof and wherein pharmaceutically effective carrier is selected from the group consisting of intradermal and transdermal carriers such as water, organic compounds or mixtures thereof, liposomes, nanosomes, nanoparticles, micelles, transfersomes, multi-lamellar vesicles, and/or other pharmaceutical carriers and wherein pharmaceutically effective carrier is selected from the group consisting of water, alcohol, organic compounds, steroids, oils, lipids and phospholipids and wherein pharmaceutically effective carrier does not require oil in the carrier and wherein pharmaceutically effective carrier is substantially free of a skin penetration enhancer or an initiator compound and wherein said therapeutic composition further includes one or more emollients, skin conditioning agents, pH stabilizing agents, humectants, buffering agents, viscosity adjusting agents, preservatives, chelating agents, emulsifying agents, conditioning agents, thickening agents, wetting agents, antioxidants, UV stabilizers, UV radiation absorbers, sun-protecting ingredients, hyaluronic acid and other cosmetic acids, proteins, botulinum toxin, micronutrients, minerals and/or vitamins and their derivatives, proteins, steroids or stimulants, biologic ingredients, stem cells, fragrances, flavors or colorants.

9. A method of treating and/or preventing a medical condition in a patient in need thereof according to claim 5, wherein said non-thermal plasma application enhances the delivery or induction of said active ingredient to the skin of said patient.

10. A method of treating and/or preventing a medical condition in a patient in need thereof according to claim 4, wherein said non-thermal plasma application enhances the delivery or induction of said therapeutic composition to the skin of said patient and wherein said non-thermal plasma application enhances the delivery or induction of said pharmaceutical carrier to the skin of said patient.

11. A method of treating and/or preventing a medical condition in a patient in need thereof according to claim 1, wherein said medical condition is selected from the group consisting of acne, psoriasis, and eczema, vitiligo, dermatitis, superficial lesions, actinic keratosis, seborrheic keratosis, lentigos, anti-aging including wrinkles, rhytides, pigmentation, redness, skin texture, tightness, scarring, pigmentation issues such as uneven pigmentation, melasma, pigmented lesions and tattoos, rebuilding collagen, elastin and overall skin rejuvenation; hair follicles and melanin stimulation or retardation of growth; fat and cellulite; vascular lesions such as birth marks, facial veins and rosacea, spider and varicose veins.

12. A method of treating and/or preventing a medical condition in a patient in need thereof according to claim 1, wherein said non-thermal plasma is administered to said patient in a single application or in multiple applications.

13. A device for treating and/or preventing a medical condition in a patient in need thereof, said device being configured for application of said non-thermal plasma in a method according to claim 1.

14. A pharmaceutical combination, said pharmaceutical combination comprising (i) a device configured for application of said non-thermal plasma in a method according to claim 1; and (ii) said therapeutic composition.

15. A method of treating and/or preventing a medical condition in a patient in need thereof according to claim 1, wherein application of said non-thermal plasma to the skin of said patient results in reduced side effects compared to application of thermal plasma to the skin of said patient and wherein application of said non-thermal plasma to the skin of said patient is non-ablative.

16. A method of treating and/or preventing a medical condition in a patient in need thereof according to claim 1, wherein said medical condition is selected from the group consisting of: dermatological conditions, disorders and diseases, bone-related disorders and diseases including osteopenia, osteomalacia, osteoporosis, vitamin and nutritional disorders, autoimmune disorders or diseases including multiple sclerosis, fibromyalgia, rheumatoid arthritis, Graves disease and lupus, periodontal disorders and/or diseases; chronic pain; vascular disorders; seasonal affective disorders; cognitive impairment; depression; diabetes; chronic renal disease; cardiovascular and metabolic disorders and/or diseases; certain types of cancers including breast cancer, prostate cancer, colon cancer, pancreatic cancer and skin cancer.

* * * * *